United States Patent [19]

Michelson

[11] Patent Number: 5,059,194

[45] Date of Patent: Oct. 22, 1991

[54] CERVICAL DISTRACTOR

[76] Inventor: Gary K. Michelson, 438 Sherman Canal, Venice, Calif. 90291

[21] Appl. No.: 478,940

[22] Filed: Feb. 12, 1990

[51] Int. Cl.$^5$ .............................................. A61B 17/60
[52] U.S. Cl. ......................................... 606/61; 606/53; 606/54; 606/57; 606/58
[58] Field of Search .................... 128/20, 89, 845, 846, 128/852, 856; 604/11, 14, 15, 16, 106, 107, 108, 109, 187; 606/53, 63, 68, 70, 102, 104, 191, 198, 216, 54–61, 72–73, 87, 90; 433/140

[56] References Cited

U.S. PATENT DOCUMENTS

| | | | |
|---|---|---|---|
| 1,137,585 | 4/1915 | Craig | 433/140 |
| 2,774,350 | 12/1956 | Cleveland | 606/54 |
| 3,486,505 | 12/1969 | Morrison | 606/61 |
| 3,709,219 | 1/1973 | Halloran | 606/57 |
| 3,750,652 | 8/1973 | Sherwin | 606/90 |
| 4,271,832 | 6/1981 | Evans et al. | 606/57 |
| 4,600,000 | 7/1986 | Edwards | 606/54 |
| 4,628,921 | 12/1986 | Rousso | 606/54 |
| 4,848,327 | 7/1989 | Perdue | 606/54 |
| 4,957,495 | 9/1990 | Kluger | 606/61 |
| 4,968,316 | 11/1990 | Hergenroeder | 606/58 |

Primary Examiner—Randall L. Green
Assistant Examiner—Anthony Paul Zuttarelli
Attorney, Agent, or Firm—Lewis Anten

[57] ABSTRACT

An improved four-legged distractor with multiplanar adjustability facilitates intervertebral bone grafting. The legs are slidably fixed to a rectangular frame so that the space between opposing legs and the space between adjacent legs may be varied. The bottom portion of each leg is offset so that a large space is created between the top portion of the legs to permit easy access to the operating space.

8 Claims, 2 Drawing Sheets

FIG. 1
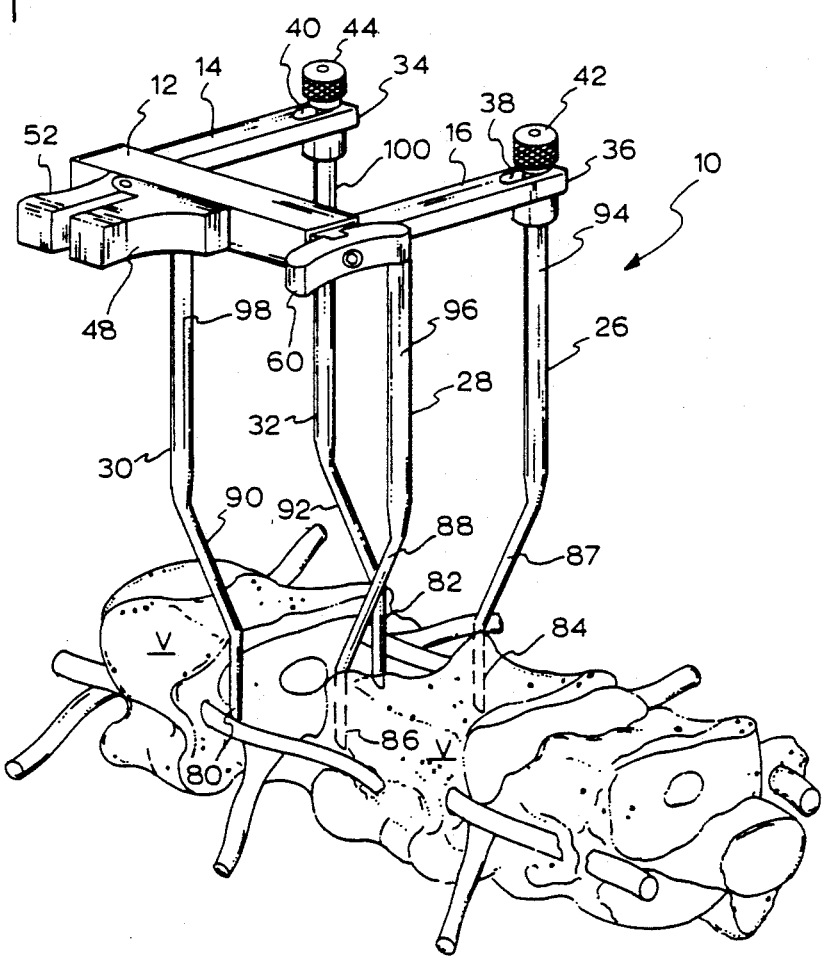
FIG. 11
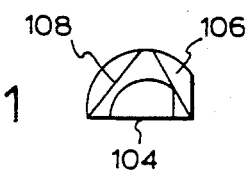
FIG. 12
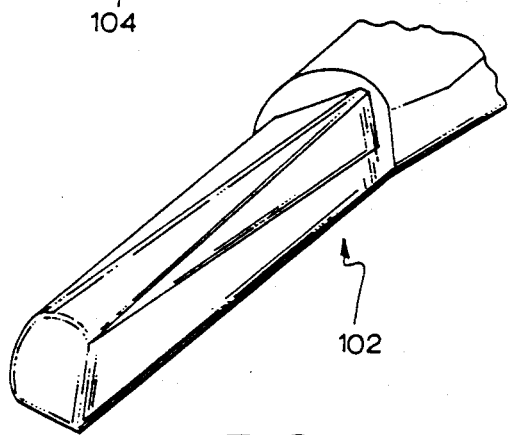
FIG. 2

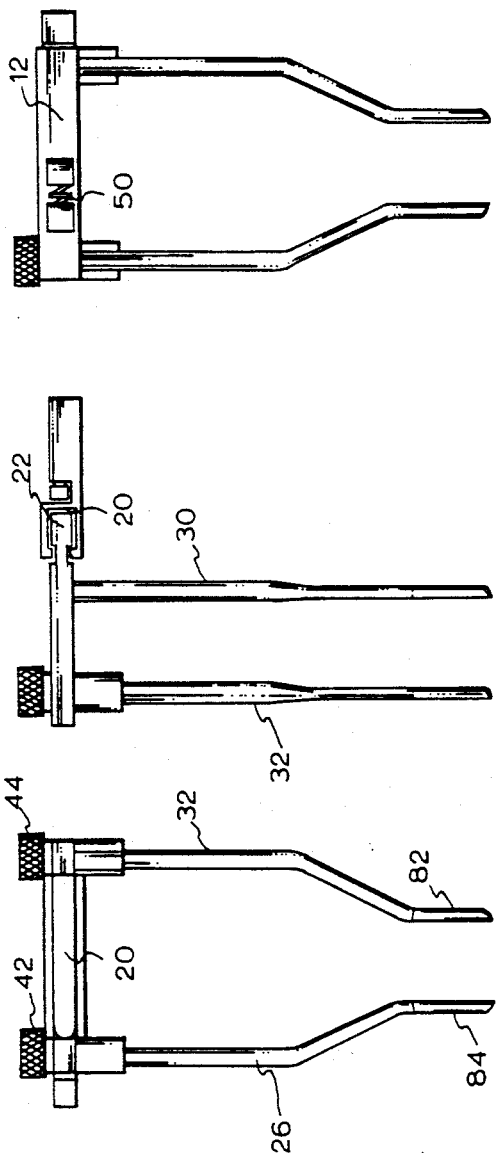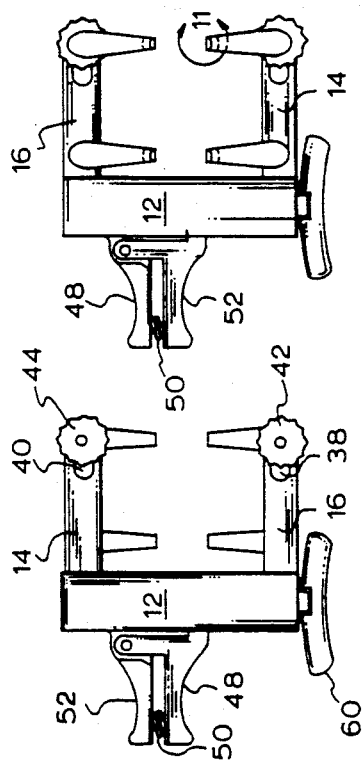

CERVICAL DISTRACTOR

BACKGROUND

Symptomatic cervical disc disease is commonly treated by an extensive anterior excision of the affected disc and its replacement with a similarly shaped iliac bone graft. Removal of the sick disc allows the interspace, the area previously occupied by the disc between two adjacent vertebrae, to collapse. Since the graft depends on proper shaping and an interference fit for its stability, the interspace must be distracted beyond its original height to assure an adequately tight fit.

Distraction of the interspace is presently achieved in one of three ways:

1. Traction—This generally requires that an ice-tong like device ("Gardner Wells Tongs" or equivalent) be rigidly connected to the patient's skull by oppositely applied penetrating metal screws. This leaves unsightly holes in the patients head and may introduce a dangerous infection. Furthermore, when traction is applied, very high loads are required because the pull is diffused at every level of the cervical spine, as well as between the skull and the spine, significantly diminishing the effectiveness of the pull at the required level. Not infrequently, the load required will result in the tongs being torn from the skull and through the scalp and face, causing grave injury. While some have attempted to achieve skull traction using various slings and harnesses, they have generally proven both ineffective and equally dangerous.

2. Spreader—It is possible to drill holes into the vertebrae above and below the interspace, and to insert screws therein. A "Casper spreader" device then engages the screws and attempts to push them apart. The screws must pass entirely through the vertebral bodies risking injury to the vital structure or they may tear from the bone risking vertebral fracture and great bodily harm. Unfortunately, placing such screws entirely through the vertebral bodies has been rejected by most doctors as it places the intimately proximate spinal cord at unjustifiable risk. Physicians have further rejected this device since hemorrhaging may follow the removal of the screws.

3. Intervertebral distractors. There are essentially two types of intervertebral distractors. The "Cloward-type" is a ratcheted instrument that opens with a scissor-like movement and which may be placed directly into the interspace, thereby allowing for the highly effective and relatively atraumatic distraction of the interspace. Unfortunately, however, the tips of such distractor engaging the adjacent vertebrae are wide relative to the size of the interspace and tend to sit away from the curved profile of the bone occurring laterally. In general, the available bone grafts, iliac in origin, tend to be almost as wide as the available disc space. Therefore, it is generally not possible to fit both the spreader and the replacement graft into the interspace at the same time. Merely thinning the legs so that they would occupy less space has been tried, and does not work, as even if the remaining leg is sufficiently strong, the thinned profile of the tip tends to cut through and fracture the bone, rendering the device neither safe nor effective.

The second type of intervertebral distractor is typified by the "Karlin Spanner/Distractor", a slender feeler gauge-like device which is turned on edge to hold the space open. Unfortunately, the thin profile tends to cut into the bone, while its placement far laterally results in an asymmetric distraction of the interspace. In general, the disc space is not able to accommodate a spanner on either side and yet allow adequate access for the insertion of the bone graft.

It is therefore apparent that a great need exists for a safe and effective cervical distraction means which ideally would be non-penetrating in its use.

SUMMARY OF THE PRESENT INVENTION

The present invention employs two pairs of depending legs which are slidably affixed to parallel arms of a support frame. The legs move in pairs and the space between the opposing pairs of legs are adjustable. This allows for the uniform distraction of the interspace. The four-point contact from the legs provides for a large surface area over which to distribute the load without injuring the bone. Because the space between the legs can be spread and then fixed, the legs can be forced far laterally onto the curvilinear portion of the bone which is a remarkably hard and strong cortical bone, thus well able to withstand the forces of distraction.

The tips of the legs themselves are offset to permit increased access to the interspace so as to facilitate the introduction of the instruments utilized in the graft placement and the insertions of the graft itself.

The tips of the legs when closed are sufficiently small and constitute a somewhat bullet-shaped end so as to facilitate their introduction into the interspace. The tips are quite rigid and slightly splayed at rest to assure that the space will be equally distracted both front and back. The tips of the legs are also offset from the upper portion of the leg to prevent over penetration of the tips into the interspace. The tips are also shaped to fit against the curvilinear bone to which they are applied. Since no part of the distractor engages the graft itself, the distractor is easily removed after insertion of the graft placement.

The distractor is opened by use of a ratchet mechanism. One skilled in the art of spinal surgery is able to assess, by feel, the appropriate tension applied to the distractor by the vertebrae and thereby the optimal distraction of the interspace. It is possible to incorporate a scale or gauge for determining such forces.

OBJECTS OF THE INVENTION

It is an object of the present invention to provide a distractor that is simple to use.

It is another object of the present invention to provide a distractor that is simple to manufacture.

It is yet another object of the present invention to provide a distractor that permits increased access to an operating space.

It is an object of the present invention to provide a distractor that is safer to use.

These and other objects of the present invention will be evident from a review of the following specification and accompanying drawings.

BRIEF DESCRIPTION OF THE DRAWINGS

FIG. 1 is a top perspective view of the distractor of the present invention show in the interspace.

FIG. 2 is a bottom view of an interspace showing the tips of the legs of the distractor in the interspace.

FIG. 3 is a right side view of the distractor.

FIG. 4 is a rear view of the distractor.

FIG. 5 is a left side view of the distractor.

FIG. 6 is a front view of the distractor.
FIG. 7 is a top view of the distractor.
FIG. 8 is a bottom view of the distractor.
FIG. 9 is a top view of the distractor with the legs in the closed position.
FIG. 10 is a side view of the distractor with the legs of the distractor in a closed position.
FIG. 11 is an end view of the tip of a leg.
FIG. 12 is an expanded view of the tip of one of the legs of the distractor.

DETAILED DESCRIPTION OF THE DRAWINGS

Referring to the figures the distractor of the present invention is referred to generally by the numeral 10. The distractor 10 comprises a frame, consisting of a main support bar 12, a pair of opposing parallel arms 14 and 16 mounted perpendicular to the support bar 12. Arm 14 is movable perpendicular to the main support bar 12 and the other, arm 16 is fixed. One end 18 of movable arm 16 is fitted within a slot 20 in the main support bar and attached to ratchet bar 22 movable within the support bar 12 along its longitudinal axis.

Arm 14 and 16 have depending legs 26, 28, 30 and 32, mounted substantially perpendicular to the arms 14 and 16 at opposite ends of the arms 14 and 16. Each of the arms 14 and 16 at their distal ends 34 and 36 has a slot 38 and 40 extending through the arms 14 and 16. The upper end of legs 32 and 26 have a narrowed rectangular portion at their top that fits within the slot for sliding movement within the slot 38 and 40 with a threaded portion extending above the arms 14 and 16. An enlarged knurled knob 42 and 44 is fitted on the threaded end of the portion of the leg that extends through the slot 38 and 40 so the knurled knob 42 and 44 may be tightened to prevent movement of the legs 26 and 32 and fix the legs relative to the arms 14 and 16.

The ratchet bar 22 has a flat gear 46 along one side for engagement with a pivotable detent 48. The detent 48 is spring biased by spring 50 between detent 48 and fixed projection 52 extending from support bar 12. The detent 48 engages the gear 46 and prevents the ratchet bar 22 from moving in both directions so that it is held in place against return to its original position. A curved thumb support member 60 depends from the end of the ratchet bar 22, fixed substantially perpendicular to the end of the ratchet bar 22.

The legs 26-32 are thin strong metal, such as steel. The lower portion 80-86 of the legs 26-32 are offset through a sloped portion 87-92 so that the lower portions 80-86 of the legs 26-32 are parallel to the central axis of the upper portion 84-100 of the legs 26-32. The lower portions 80-86 of the legs 26-32 are oriented so that their central axis is closer to the opposite legs than the central axis of the upper portion of the legs.

Referring to FIGS. 11 and 12, a tip 102 of the legs is shown in detail. The tip 102 has a flat portion 104 on the inside of the leg and a narrowed portion on the opposite side formed by sloped surfaces 106 and 108. The tip forms a small profile for ease of entry into the interspace. When the distractor 10 is closed, the flattened portion 104 of the tips are flush with one another.

Referring to FIG. 1 the interspace distractor is shown in the interspace between two vertebrae V in its open position. As shown, the tips of the legs are parallel to one another so that, as shown in FIG. 2, the tips 102 are positioned outside of the cervical space. The large space formed at the top of the distractor between the arms 14 and 16 and the support bar 12 permits easy access into the cervical space. This is larger than the space that would be created absent the offset of the legs.

The distractor 10 is used as follows: The surgeon would make the incision and open up the cervical interspace and the tips of the distractor would be inserted into the space. The separation of the movable legs would be determined and they would be moved within slots 38 and 40 until the proper size was obtained. The knurled knobs would then be turned until the legs were fixed relative to their arms. The distractor would be held in one hand and the thumb of the other hand would be placed on the curved portion 60 on the movable ratchet bar 22 with the index finger placed on the extension 52 extending from the support bar 12. The surgeon would then push on the curved thumb member 60 and simultaneously pull on the extension 52 gradually opening or spreading the legs 26-32 of the distractor 10 apart.

The ratchet bar 22 permits the distractor to be separated and be held in its open position. As the ratchet bar continues to separate the legs, tension from the discs operates on the legs. The surgeon can feel the degree of resistance that is encountered by the additional efforts to separate the legs of the distractor and from experience can determine the optimum degree of separation required.

While in the preferred embodiment it is believed that the pressure and amount of separation that is required to exert will be evident to a skilled surgeon, it is possible to use pressure gauges or scales built into the distractor so that the pressure being applied to the legs of the distractor can be visually displayed, either as a range by use of lights, or the display of the specific pressures being applied. Also, in the same manner, various measuring devices can be employed that would indicate the distance that the distractor has its legs separated. This may be by an electrical device or appropriate markings or colors on the distractor. However, it is not believed that either of the above expedients would be necessary for the employment of the device.

As can be seen in FIG. 1 the amount of room that the surgeon has to operate in the disc space is largely unimpaired by the presence of the distractor. The difference in space available for introducing instruments is graphically illustrated by comparing the amount of space that is present at the top of the distractor compared with the space that is present at the tips of the legs. Thus, the presence of the offset contributes greatly to the ease of introducing instruments into the disc space.

When the operation has been completed, the detent is disengaged by pivoting of member 48, causing the detent to disengage from the gear 46. This permits the pressure that is applied to the legs of the distractor by the vertebrae V to cause the legs of the distractor to come together slightly so that the distractor 10 can be removed from the interspace.

While the present invention has been specifically described in regard to the cervical spine, it is anticipated that it would with changes in the relative proportions and alterations, work equally well throughout the spine.

It is anticipated that a four-point distractor could be constructed by various other means, including but not limited to the following. The distractor itself could have two depending legs extending form the support arms and then a pair of tips would be connected to each said legs, each having two points of contact to the bone.

These tips would come at a predetermined width, eliminating the need for the adjustability of the width.

In the preferred embodiment of the invention the support bar is about 1¾ inches long and the two arms are about 1¼ inches long. The legs are 3 inches long, with the upper portion of the leg being 1½ inches and the lower portion about ½ inches. The angle of the transition form the upper portion of the leg to the lower portion of the leg is about 30 degrees. The length of the lower portion and the offset prevents the legs from over penetrating the interspace. While it is appreciated that these are the preferred dimensions for a cervical distractor it is appreciated that the dimensions of the device would be varied for use in other locations of the body. It is also appreciated that other modifications of the invention may be made with out departing the scope and concept of the present invention and it is intended that they be incorporated within the scope of this invention.

What I claim is:

1. A spinal distractor comprising a frame having a support bar and having a pair of arms extending perpendicular from said support bar, one of said arms fixed in relationship to said support bar and the other of arms being movable in relationship to said support bar, a pair of opposing legs dependent from each of said arms, at least one of said legs of each pair of said legs fixed in relationship to said arm, said legs having an upper portion having a central axis and a lower portion having a central axis and an angled portion intermediate said upper and lower portions whereby the central axis of the lower portion of said legs is parallel to the central axis of the upper portion.

2. The spinal distractor of claim 1 further comprising a ratchet member movably coupled within said support bar and at least one of said arms being attached to said ratchet member wherein actuation of said ratchet member selectively displaces the arm in one direction along the support bar.

3. The spinal distractor of claim 2 in which said ratchet member has a detent movable between a first position and a second position said detect engaging a gear on said ratchet member, permitting said arm to be able to move in more than on direction along said support bar.

4. The spinal distractor of claim 3 in which the legs of said distractor are flat on at least one side of said legs.

5. The spinal distractor of claim 1 in which one of each pair of legs are movably coupled to each of said arms.

6. A spinal distractor comprising a frame having a support bar and having a pair of arms extending perpendicular from said support bar, at least one of the arms being movable in relationship to said support bar, a pair of opposing legs dependent from each of said arms, said legs having an upper portion having a central axis and a lower portion having a central axis and an angled portion intermediate said upper and lower portions whereby the central axis of the lower portion of said legs is parallel to the central axis of the upper portion said movable arm is attached to a ratchet member movable within said support bar for selectively limited movement of said arm in one direction and further comprising a ratchet member movably coupled within said support bar and at least one of said arms being attached to said ratchet member wherein actuation of said ratchet member selectively displaces the arm in one direction along the support bar.

7. The spinal distractor of claim 2 in which said ratchet member has a detent movable between a first position and a second position said detent engaging a gear on said ratchet member, permitting said arm to be able to move in more than on direction along said support bar.

8. The spinal distractor of claim 7 in which the legs of said distractor are flat on at least one side of said legs.

* * * * *